United States Statutory Invention Registration [19]

[11] Reg. Number: H406

Wohltjen [43] Published: Jan. 5, 1988

[54] ORGANOPHOSPHORUS SELECTIVE ION MOBILITY SPECTROMETER

[75] Inventor: Henry Wohltjen, Burke, Va.

[73] Assignee: United States of America, Washington, D.C.

[21] Appl. No.: 581,398

[22] Filed: Feb. 17, 1984

[51] Int. Cl.[4] ..... C12P 7/32

[52] U.S. Cl. ..... 436/153; 422/54; 436/106; 436/103; 436/114

[58] Field of Search ..... 422/50, 54, 83, 88, 422/90, 98; 250/423 R, 424, 425, 286, 287; 436/153, 106, 114, 103

[56] References Cited

U.S. PATENT DOCUMENTS

| | | | |
|---|---|---|---|
| 2,550,498 | 4/1951 | Rice . | |
| 3,589,869 | 6/1971 | Scolnick . | |
| 3,845,301 | 10/1974 | Wernlund et al. | 250/287 |
| 3,850,579 | 11/1974 | Dubsky | 422/54 |
| 3,864,575 | 2/1975 | Hashmi et al. . | |
| 4,203,726 | 5/1980 | Patterson | 422/54 |
| 4,311,669 | 1/1982 | Spangler | 422/98 |

OTHER PUBLICATIONS

Patterson, "Selective Responses of Flameless Thermionic Detector" *Journal of Chromatography* 1978, No. 167, pp. 381-397, CA 90(16): 132332 C.

Patterson, "Thermionic Nitrogen-Phosphorous Detection With an Alkali-Ceramic Bead" *J. Chromatogr. Sci.* 16(7), pp. 275-280 (1978).

J. P. Carrico et al., "Simple Electrode Design For ION Mobility Spectrometer" Journal of Physics E: vol. 16, 1983, pp. 1058-1062.

Paul L. Patterson et al., "Thermionic Nitrogen-Phosphorus Detection With An Alkali-Ceramic Bead" Journal of Chromatographic Science, vol. 16, Jul. 1978, pp. 275-280.

J. A. Lubkowitz et al., "Preparation And Characterization Of Glass Beads For Use In Thermionic Gas Chromatolgraphic Detectors" Analytical Chemistry, vol. 50, No. 4, Apr. 1978, pp. 672-676.

*Primary Examiner*—John F. Terapane
*Assistant Examiner*—Susan Wolffe
*Attorney, Agent, or Firm*—John L. Forrest

[57] ABSTRACT

An ion mobility spectrometer for analysis of a gaseous sample wherein only nitrogen and phosphorus containing molecules of the sample are ionized. The spectrometer is of the type having an ion source for ionizing the sample gas and a shutter for gating ions into a drift region, wherein an electric field gradient exists. The ion source includes a bead which comprises a thermally stable material, such as a ceramic or glass, having an alkali metal compound on its surface. The bead is immersed in a gaseous mixture of hydrogen and air, and is heated to a temperature of 200°-1000° C. The bead selectively ionizes phosphorus and nitrogen containing molecules of the sample upon contact with the bead.

17 Claims, 3 Drawing Figures

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

ORGANOPHOSPHORUS SELECTIVE ION MOBILITY SPECTROMETER

BACKGROUND OF THE INVENTION

This invention relates to spectrometry, and more particularly to ion mobility spectrometry.

Ion mobility spectrometry is an extremely sensitive method for detecting small quantities of vapor. Typically, the technique requires that the ambient air to be monitored be drawn over a dimethyl silicone membrane to separate the trace organic molecules to be detected from other atmospheric constituents such as water vapor etc. This enriched vapor is then passed into a small ionization chamber where the vapor is bombarded with either beta particles (typically from $Ni^{63}$ source) or alpha particles (typically from an $Am^{241}$ source). The ions thus formed are drawn into a drift tube by applying a brief electrostatic field across the ionization source. Once in the drift tube, the ions are accelerated by a linear electric field gradient applied along the length of the tube. Heavy ions achieve a slower drift velocity than lighter ions and are thereby separated. The ions reaching the end of the drift tube strike a metal collector electrode and the resulting ionic current is amplified by an electrometer. Thus, an ion mobility spectrum is produced by measuring the ion current versus time after admitting the ion pulse into the drift tube.

The ion mobility spectrometer is analogous, in some ways, to a time of flight mass spectrometer except that the ion mobility spectrometer operates at atmospheric pressure. Ion mobility spectra have much lower resolution and have peak positions which are dependent on the concentration of the ions as well as their type. Ion mobility spectrometers are extremely sensitive with part per trillion level detection limits for some compounds. Furthermore, they offer qualitative information about the constituents of the vapor being monitored.

Prior ion mobility spectrometers as described above, however, have one important weakness. The spectra produced are not always unique for a particular vapor because of the complex ion-molecule chemistry which can occur in the source prior to injection into the drift tube. Much of this problem is caused by the alpha or beta radioactive ionization sources which are not adequately selective in their operation. If a complex mixture of vapors is being analyzed then a very complex spectrum can result which may easily obscure the detection of the desired component. More particularly, in regard to the detection of toxic organophosphorus compounds, prior ion mobility systems can be confused by pollutant interference vapors present in high concentration (e.g. diesel exhaust) having the same molecular masses as vapors to be detected, thereby resulting in a high false alarm rate and unacceptable signal to noise ratios.

SUMMARY OF THE INVENTION

It is, therefore, an object of the present invention to provide an ion mobility spectrometer having a relatively low false alarm rate in respect to interference vapors.

It is also an object of the present invention to provide an ion mobility spectrometer having an improved immunity to interference vapors over prior spectrometers, and thus, an improved signal to noise ratio.

The above objects are realized in an ion mobility spectrometer that includes a thermionic alkali-activated contact ionization source which selectively ionizes only nitrogen and phosphorus compounds. The ion mobility spectrometer of the present invention is of the type having an ion source for ionizing a sample gas, thereby producing ions, and wherein the ions are gated by a shutter along a predetermined path into a drift region having an electric field parallel to the ion path. The spectrometer according to the present invention includes an ion source comprising a body, immersed in a mixture of air and hydrogen, which includes a thermally stable material having an alkali metal compound on its surface. In addition, the body is heated to a temperature of from 200°-1000° C. When a sample gas comes into contact with the body, phosphorus and nitrogen containing molecules are selectively ionized.

Since the ion source in the spectrometer is nitrogen-phosphorus selective, various interference vapors not containing nitrogen or phosphorus are not ionized. Therefore these ions, whose detection is not desired, are not detected, thereby lowering the false alarm rate and improving the signal to noise ratio.

DESCRIPTION OF THE PREFERRED EMBODIMENTS

An ion mobility spectrometer is described herein, which employs a nitrogen-phosphorus compound selective thermionic contact ionization source, wherein the source includes an alkali activated bead, described in more detail below.

Figure 1:
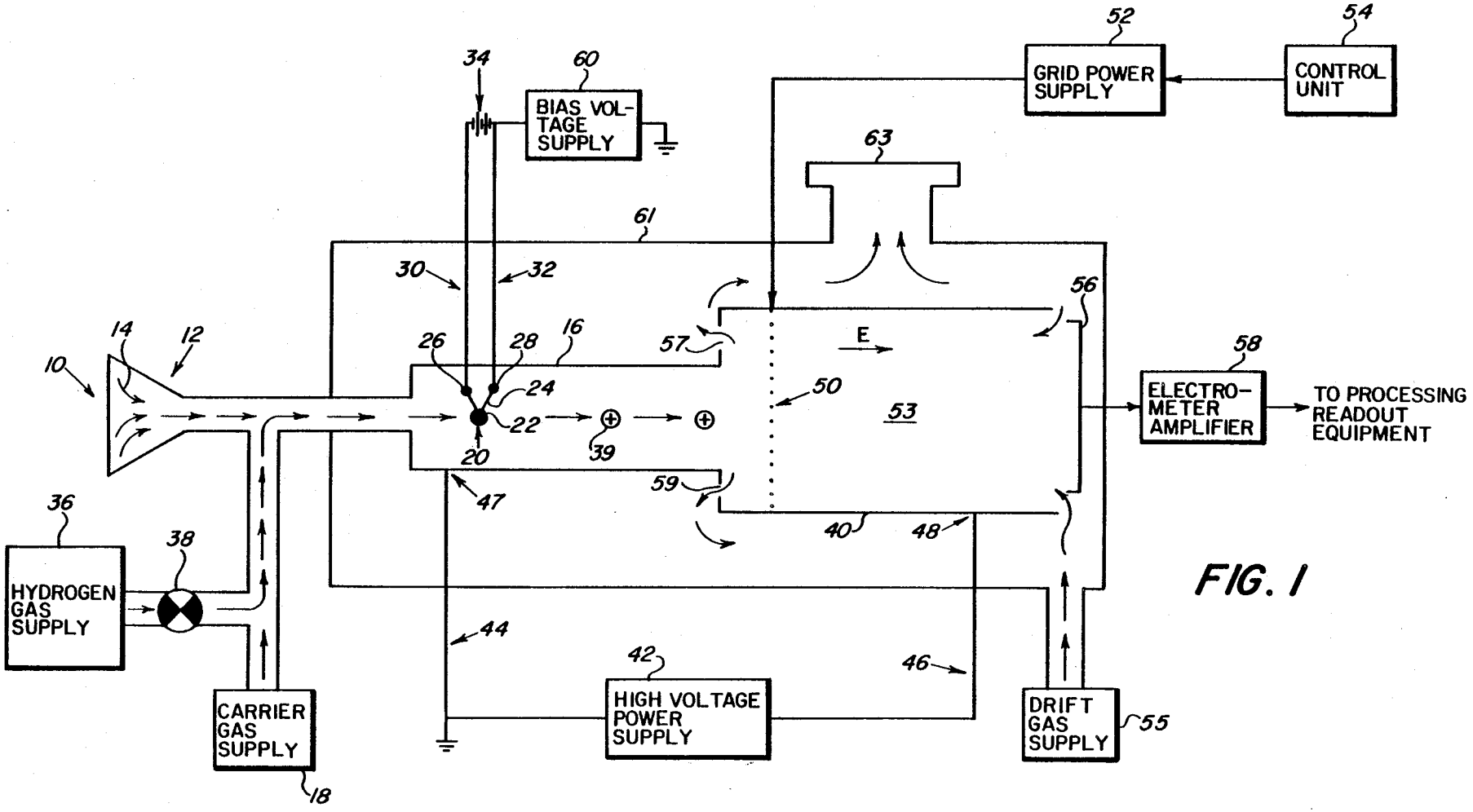
FIG. 1 is a schematic representation of an ion mobility specrometer according to the present invention having an ion source for selectively ionizing phosphorous an nitrogen containing molecules.

Referring now to FIG. 1, a schematic representation of an ion mobility spectrometer according to the present invention is shown. The spectrometer preferably includes a membrane 10 mounted on the end of conduit 12. Membrane 10 may be, by way of example. dimethyl silicone, microporous polypropylene, or OV 101 impregnated Celgard. A sample gas, ambient air for example, is admitted through membrane 10 into conduit 12, the flow of the sample gas being denoted by arrows at 14. Trace molecules to be detected are separated by membrane 10 from other atmospheric constituents such as water vapor. Thus, some unwanted atmospheric constituents are not allowed to pass into conduit 12. As will be apparent to one skilled in the art, employing the membrane 10 in the spectrometer shown in FIG. 1 is a preferred but optional feature, which serves to improve the performance of the device by filtering out molecules that are not to be detected. The sample gas is carried by a suitable carrier gas, such as air, nitrogen, helium or argon, to ionization chamber 16. As shown, the carrier gas is supplied by carrier gas supply 18 at a flow rate of, for example, about 10-500 ml/min. In addition, it should be understood that the carrier gas may be omitted, providing some means is provided, such as a pump, to move the sample gas to ionization chamber 16.

The sample gas and carrier gas mixture flows into ionization chamber 16 as shown, so as to impinge on ion source 20 disposed within ionization chamber 16 in the path of the gas flow. Supporting structures for ion source 20 have been omitted for clarity of illustration. Ion source 20 comprises a bead 22 and metallic filament 24 embedded within the bead. Filament 24 is connected to leads 30 and 32 at connection points 26 and 28, which may be by way of example, spot welds. Power supply 34, preferably a D.C. current supply, provides a current flow via leads 30 and 32 to filament 24. Accordingly, filament 24 heats up, and consequently heats bead 22. Additionally. hydrogen gas supply 36 is provided to supply a flow of hydrogen gas to ionization chamber 16, such that bead 22 is immersed in a mixture of hydrogen gas and air. Bleed valve 38 may be adjusted so as to regulate the air-hydrogen mix in which bead 22 is immersed. Typically, hydrogen gas flow is regulated so that the flow rate from hydrogen gas supply 36 is about 0.1%-2% of the carrier gas flow rate from carrier gas supply 18.

Ion source 20 functions so as to selectively ionize only phosphorus and nitrogen containing molecules of the sample gas by means of alkali activated contact ionization. The structure and operation of ion source 20 will be discussed in detail below in reference to FIGS. 2 and 3.

Ions, as shown at 39, formed at ion source 20 and the gaseous mixture of air and hydrogen may pass from ionization chamber 16 into drift tube 40. The inner surfaces of ionization chamber 16 and drift tube 40 are coated in the illustrated embodiment with a resistive ink (not shown) utilized in the generation of an electric field within chamber 16 and tube 40 as will be described below. One example of a suitable resistive ink is DuPont 9519, although any similar resistive ink would be suitable.

High voltage power supply 42 is provided to apply potentials to the resistive ink coating at opposite ends of ionization chamber 16 and drift tube 40 via leads 44 and 46. Since positive ions to be detected are produced by ion source 20 as discussed below a positive potential is applied to a contact point 47 in ionization chamber 16, and a negative potential is applied to a contact point 48 in drift tube 40. Contact points 47 and 48 may be provided by a thick film conductor ink (not shown), DuPont 6120 for example, painted on the inner surface of ionization chamber 16 and drift tube 40. The thick film conductor ink is appropriately fired to provide an excellent contact surface for leads 44 and 46. Typically, potentials are applied to contact points 47 and 48 such that an electric field is generated within ionization chamber 16 and drift tube 40 of about 50-500 V/cm.

Alternatively, an electric field may be generated by metallic rings mounted concentrically with respect to chamber 16 and drift tube 40. In this arrangement, the rings are connected in series and potentials are applied to the end rings in a manner similar to that described above. It is emphasized, however, that any means of achieving the necessary electric field within chamber 16 and drift tube 40 would be suitable in accordance with the present invention.

Thus, the electric field produced within the ionization chamber 16 is an axial field which acts to accelerate ions formed at ion source 20 along a predetermined path into drift tube 40. The gas flow within chamber 16 also serves to carry ions into drift tube 40. As ions enter drift tube 40, they are received by shutter grid 50, described below. Similarly, an electric field is generated in drift tube 40 which is parallel to the predetermined path of the ions.

Shutter grid 50 is of conventional design, and comprises a metallic wire mesh mounted within drift tube 40. Grid power supply 52 supplies a negative potential to shutter grid 50 in its normally closed condition. In the closed condition, the grid 50 is closed to the passage of positively charged ions from ionization chamber 16 since the negative grid acts to attract positive ions to its surface. In the grid open condition, however, no potential is applied to shutter grid 50. Thus, in this open condition, shutter grid 50 allows ions to pass into drift region 53. Here, the drift region is defined as that region in drift tube 40 between shutter grid 50 and the collector plate, hereinafter described. The above mentioned conditions are controlled by means of control unit 54. Control unit 54 includes an electronic clock which generates trigger pulses at predeteremined intervals which are coupled to grid power supply 2. In response to a trigger pulse, grid power supply 52 cuts off its input to shutter grid 50 to open grid 50 and thereby allow ions to pass into drift region 53. Thus, sequential application of trigger pulses to grid power supply 52 acts to open the gate at certain intervals. A typical trigger pulse rate is for example 100 per second. In addition, a typical gate width is about 10 microseconds to 10 milliseconds, wherein gate width is defined as the amount of time the shutter grid is open for each trigger pulse when transmitting ions into the drift region. The effect of the periodic opening of grid 50 is to cause pulses of bunched ions to enter drift region 53. The instrument is operated in a pulsed mode because continuous ionization and acceleration would lead to a continuous output with intractable overlapping of various masses.

As an alternative to the mesh type shutter grid shown in FIG. 1. the grid may be simply a single wire if the drift tube has a small cross sectional area of, for example, a square centimeter.

A drift gas, such as nitrogen or air, is injected into drift region 53 by drift gas supply 55 in a direction so as to oppose the flow of the gaseous mixture flowing into drift tube 40 from chamber 16. The drift gas flow helps to insure a constant drift resistance for ions passing through drift region 53. In addition, the flow of drift gas tends to oppose the flow of nonionized molecules entering drift region 53, and thereby force such gas molecules out ports 57 and 59. Thus, the drift gas flow assists in preventing ion-molecule reactions which might produce ions well within drift region 53. Such ion formation will result in drift times not in accordance with the true masses of the ions formed. Consequently, utilization of the drift gas enhances the resolution of the illustrated embodiment, but is an optional feature not critical to device operation.

A collector plate 56, which may be, by way of example, a Faraday cup, is positioned to receive ions after they have drifted through drift region 53. The output of collector 56 is coupled to an electometer amplifier 58, which appropriately amplifies the signal from collector 56.

An additional preferred feature included in the embodiment of FIG. 1 is a bias voltage supply 60 for applying a potential to ion source 20 which is positive with respect to the potential at collector plate 56. This feature assists in the movement of positive ions from ion source 20 to collector 56.

As shown, the spectrometer illustrated in FIG. 1 also includes an envelope 61, which encloses ionization chamber 16, drift tube 40, and collector plate 56. All gases accumulating in envelope 61 may exit through an exit port 63.

In normal operation, the spectrometer shown in FIG. 1 performs as follows. A sample gas 14 is allowed to enter through membrane 10. The sample gas 14 is then carried along conduit 12 by a carrier gas, and enters ionization chamber 16 so as to flow around ion source 20. Upon contact with ion source 20, immersed in a mixture of hydrogen and air and maintained at a temperature of 200°-1000° C. as described below, only phosphorus and nitrogen containing sample gas molecules are ionized, yielding ions as shown at 39. These ions are accelerated along a predetermined pathway toward shutter grid 50 by the electric field gradient produced within ionization chamber 16, the ions also being carried toward shutter grid 50 in the normal flow of gases.

Control unit 54 generates a trigger pulse, as described above, which cuts off grid power supply 52 momentarily. A bundle of ions is therefore allowed to pass through opened grid 50 into drift region 53. The ions entering drift region 53 through grid 50 are accelerated toward collector 56 in response to the aforementioned field gradient, in accordance with their mobility, the more mobile ions being accelerated faster and thus reaching collector 56 before less mobile ions. The ions do not tend to fall into a continuous mobility spectrum but rather tend to fall into discrete mobility groups. Thus, groups or bundles of ions will reach collector 56 at discrete times after grid 50 is opened with the time being related to the mobility of the ions in the bundle. The ions are deionized by the collector 56 thus generating an electrical current whose magnitude is related to the number of ions instantaneously striking the collector 56. This current is amplified by amplifier 58 and may be applied in a conventional manner to various processing and readout equipment. For example, the output from amplifier 58 might be applied to a signal averager, such as a Nicolet 1160 or Digital Data PD12, whose output could be plotted as a spectrum on an X-Y plotter or other readout device.

Figure 2:
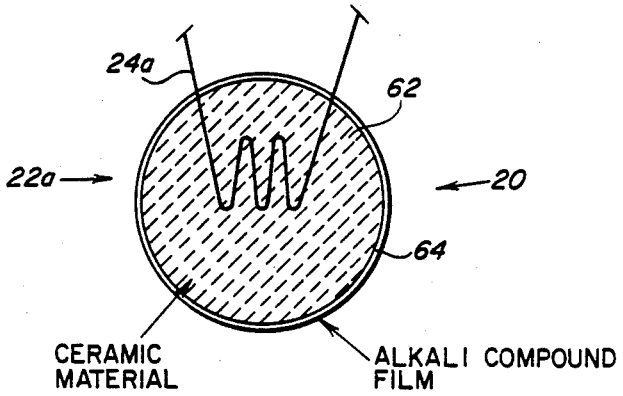
FIG. 2 is an illustration of an embodiment the ion source which employs a ceramic bead.

Referring now to FIG. 2, there is shown one embodiment of ion source 20 in greater detail, wherein ion source 20 is employed in the ion mobility spectrometer shown in FIG. 1 as explained above. Ion source 20 comprises a bead **22*a* and metallic filament 24*a* of, for example, platinum or nichrome, embedded within bead 22*a*. As noted above, filament 24*a* is supplied with current so as to heat bead 22*a*. For successful operation of ion source 20, the bead should be heated to a temperature of 200°-1000° C. this temperature range is essential to the operation of source 20 since temperatures above 1000° C. will break down phosphorus and nitrogen containing ions produced, and temperatures below the lower limit will not result in ionization of molecules coming into contact with bead 22*a*. Also as explained above, bead 22*a*** is immersed in a gaseous mixture of air and hydrogen, a feature also necessary for the desired ionization process to take place.

Bead **22*a* comprises a ceramic material 62, such as steatite, alumina, or macor, having a thin alkali compound film 64 formed on its surface. The thin alkali film 64 may be formed on the surface of the ceramic material 62 by simply dipping the ceramic material 62 in an aqueous alkali compound solution and allowing the film deposited to air dry. Examples of suitable alkali compounds for use in film 64** are NaCl, KCl, RbCl, $Na_2SO_4$, $K_2SO_4$, $NaNO_3$, $CsNO_3$, LiCl, CsCl, $LiNO_3$, or NaF.

Figure 3:
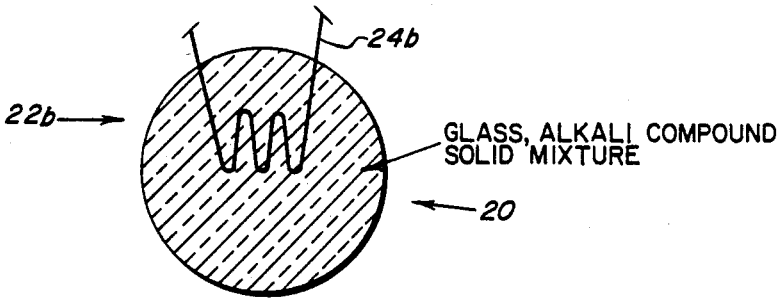
FIG. 3 shows an alternate embodiment of the ion source which includes a glass bead.

Referring now to FIG. 3, there is shown an alternatve embodiment of ion source 20 to be employed by the ion mobility spectrometer previously described. Here, ion source 20 includes filament **24*b* which is embedded in bead 22*b* in a manner similar to that described in connection with FIG. 2. Bead 22*b* comprises a solid mixture of glass and an alkali compound. Amorphous silica or Pyrex glass are examples of glasses suitable for use in bead 22*b*. Suitable alkali compounds in the FIG. 3 embodiment include NaCl, KCl, RbCl, $Na_2SO_4$, $K_2SO_4$, $NaNO_3$, $CsNO_3$, LiCl, CsCl, $LiNO_3$, and NaF. Phosphorus-nitrogen selective ionization can be achieved with bead 22*b* under the conditions already described: namely, a bead temperature 200°-1000° C. and immersion of bead 22*b*** in a gaseous mixture of hydrogen and air.

Bead **22*b* may be constructed by preparing a mixture of a suitable glass as described above, preferably in a ground form, and an alkali compound The mixture is then melted in a conventional manner, followed by the pulling of strands from the melt. A strand thus formed may then be placed in contact with filament 24*b*, followed by a temporary application of heat by means of a torch, for example. The glass and alkali compound mixture then solidify around the filament such that filament 24*b* remains permanently embedded in bead 22*b***. It should also be noted that a flux such as sodium carbonate or boric acid may be added the above mentioned mixture.

Many alternative arrangements to the above described ion source embodiment are possible according to the present invention. For example, the filament embedded in the bead may be replaced by any means for heating the bead to the desired temperatures. Examples of such heating means include a laser, a simple flame applied to the bead, etc. The filament is preferred, however, since it heats the bead to a highly uniform temperature throughout. In addition, although the bead is shown as being generally spherical in shape, any geometric shape would perform according to the present invention.

Stated more generally, the ion mobility spectrometer of the type previously described in reference to FIG. 1 employs an ion source which includes a body comprising a thermally stable material having an alkali compound formed on its surface. The body is positioned in the spectrometer so as to receive a sample gas to be analyzed, such that sample gas molecules are selectively ionized upon contact with the alkali activated body surface. A means is provided to heat the body surface to a temperature of 200°-1000° C., and the body is immersed in an air-hydrogen gaseous atmosphere.

Molecules impinging upon the surface of the bead are selectively ionized by contact ionization as follows. Molecules impact the heated, alkali-activiated surface of the bead, and are ionized by the extraction of electrical charge from the surface. This surface ionization process is controlled by the bead surface work function, the bead surface temperature, and the composition of gases surrounding the surface.

Ion source 20 acts to ionize only phosphorus and nitrogen containing compounds under the temperature and gas atmospheric conditions outlined above. Thus, various interference vapors having masses identical to nitrogen and phosphorus containing vapors to be detected are not ionized by ion source 20. Accordingly, the above mentioned interference vapors are not detected in the obtained spectrum. The spectrum obtained in accordance with the present invention is thereby relieved of many misleading interference vapor ion peaks which are indistinguishable from those peaks obtained upon detection of sample gas vapors whose detection is desired. Thus, the spectrometer is essentially immune from the confusion caused by interference vapors. In addition, the spectrometer eliminates the need for incorporating expensive ion sources into the system which require radioactive materials.

Obviously many modifications and variations of the present invention are possible in light of the above teachings. It is therefore to be understood that within the scope of the appended claims the invention may be practiced otherwise than as specifically described.

What is claimed and desired to be Secured by Letters Patent of the United States is:

1. An ion mobility spectrometer for analyzing a sample gas of the type having an ion source for ionizing the sample gas, thereby producing ions, and means for gating ions by a shutter along a pathway into a drift region having an electric field parallel to the ion pathway, the improvement wherein:

said ion source comprises a body immersed in a mixture of air and hydrogen, said body comprising a thermally stable material having an alkali metal compound on its surface, and wherein said spectrometer further comprises a heating means for heating the surface of said body to a temperature of from 200°-1000° C.; and a means for introducing the sample gas to the surface of said body; whereby only phosphorus and nitrogen containing molecules of the sample gas are ionized upon contact with the surface of said body.

2. An ion mobility spectrometer as recited in claim 1, wherein said thermally stable material is a ceramic material.

3. An ion mobility spectrometer as recited in claim 2, wherein said alkali metal compound is selected from the group consisting of NaCl, KCl, RbCl, $Na_2SO_4$, $K_2SO_4$, $NaNO_3$, $CsNO_3$, LiCl, CsCl, $LiNO_3$, or NaF.

4. An ion mobility spectrometer as recited in claim 3, wherein said heating means comprises a metal filament embedded in said body, and a power supply means for supplying electric current to said filament.

5. An ion mobility spectrometer as recited in claim 3, wherein said ceramic material is steatite.

6. An ion mobility spectrometer as recited in claim 3, wherein said ceramic material is alumina.

7. An ion mobility spectrometer as recited in claim 3, wherein said ceramic material is macor.

8. An ion mobility spectrometer as recited in claim 3, wherein a thin film of said alkali compound is formed on the surface of said ceramic material.

9. An ion mobility spectrometer as recited in claim 8, wherein said body is formed as a bead.

10. An ion mobility spectrometer for analyzing a sample gas of the type having an ion source for ionizing the sample gas, thereby producing ions, and means for gating ions by a shutter along a pathway into a drift region having an electric field parallel to the ion pathway, the improvement wherein:

said ion source comprises a body immersed in a mixture of air and hydrogen, said body comprising a thermally stable material of a solid mixture of an alkali metal compound and glass and wherein said spectrometer further comprises a heating means for heating the surface of said body to a temperature of from 200°-1000° C.; and a means for introducing the sample gas to the surface of said body; whereby only phosphorous and nitrogen containing molecules of the sample gas are ionized upon contact with the surface of said body.

11. An ion mobility spectrometer as recited in claim 10, wherein said alkali metal compound is selected from the group consisting NaCl, Kcl, RbCl, $Na_2SO_4$, $K_2SO_4$, $NaNO_3$, $CsNO_3$, LiCl, CsCl, $LiNO_3$, or NaF.

12. An ion mobility spectrometer as recited in claim 11, wherein said heating means comprises a metal filament embedded in said body, and a power supply means for supplying electric current to said filament.

13. An ion mobility spectrometer as recited in claim 12, wherein said body is formed as a bead.

14. An ion mobility spectrometer as recited in claim 11, wherein said glass is amorphous silica.

15. A method of analyzing a sample gas, comprising the steps of:

providing a body immersed in a mixture of air and hydrogen, said body comprising a thermally stable material having an alkali metal compound on its surface;

heating said body to a temperature of from 200°-1000° C.;

introducing the sample gas to the surface of said body, whereby only phosphorus and nitrogen containing molecules of the sample gas are ionized upon contact with the surface of said body, thereby yielding selected sample ions;

accelerating the selected sample ions along a predetermined path:

gating the accelerated sample ions to a drift region;

producing an electric field in the drift region, the electric field being in a direction parallel to the predetermined path: and detecting the selected sample ions after they have drifted through the drift region.

16. An ion mobility spectrometer for analyzing a sample gas comprising:

a bead immersed in a mixture of air and hydrogen, said bead comprising a ceramic material having a thin alkali metal compound film on its surface, wherein said alkali metal compound is selected from the group consisting of NaCl, KCl, RbCl, $Na_2SO_4$, $K_2SO_4$, $NaNO_3$, $CsNO_3$, LiCl, CsCl, $LiNO_3$, or NaF;

a heating source for heating said bead to a temperature of from 200°-1000° C., said heating source including a metallic filament embedded in said bead, and also including a power source means for supplying an electric current to said filament;

means for introducing the sample gas to the surface of said bead, whereby only phosphorus and nitrogen containing molecules of the sample gas are ionized uon contact with said bead, thereby yielding selected sample ions:

means for accelerating the selected sample ions along a predetermined path;

shutter means positioned to receive the accelerated selected sample ions, said shutter means gating selected sample ions to a drift region:

electric field source means for producing an electric field in the drift region, the electric field being in a direction parallel to the predetermined path;

detector means positioned to receive selected sample ions after the ions have drifted through the drift region, said detector means detecting the number of ions received.

17. An ion mobility spectrometer for analyzing a sample gas comprising:

a bead immersed in a mixture of air and hydrogen, said bead comprising a solid mixture of a glass and an alkali metal compound selected from the group consisting of NaCl, KCl, RbCl, $Na_2SO_4$, $K_2SO_4$, $NaNO_3$, $CsNO_3$, LiCl, CsCl, $LiNO_3$, or NaF:

a heating source for heating said bead to a temperature of from 200°-1000°, said heating source including a metal filament embedded in said bead, and a power supply means for supplying electric current to said filament;

means for introducing the sample gas to the surface of said bead, whereby only phosphorus and nitrogen containing molecules of the sample gas are ionized upon contact with said bead, thereby yielding selected sample ions;

means for accelerating the selected sample ions along a predetermined path;

shutter means positioned to receive the accelerated selected sample ions, said shutter means gating selected sample ions to a drift region;

electric field source means for producing an electric field in the drift region, the electric field being in a direction parallel to the predetermined path;

detector means positioned to receive selected sample ions after the ions have drifted through the drift region.

* * * * *